US00PP35522P2

(12) United States Plant Patent
Heuger

(10) Patent No.: US PP35,522 P2
(45) Date of Patent: Dec. 5, 2023

(54) ***SAXIFRAGA* PLANT NAMED 'SH 1940'**

(50) Latin Name: *Saxifraga cortusifolia*
Varietal Denomination: SH 1940

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/123,135

(22) Filed: Mar. 17, 2023

(51) Int. Cl.
*A01H 5/02* (2018.01)
*A01H 6/80* (2018.01)

(52) U.S. Cl.
USPC ..... Plt./263.1
CPC ..... *A01H 6/80* (2018.05)

(58) Field of Classification Search
USPC ..... Plt./263.1
CPC ..... A01H 6/80; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Saxifraga* plant named 'SH 1940', characterized by its broadly upright and mounded plant habit; moderately vigorous to vigorous growth habit and moderate growth rate; dark green-colored leaves; freely flowering habit; and creamy white-colored flowers that are held above the foliar plane.

2 Drawing Sheets

Figure 2:
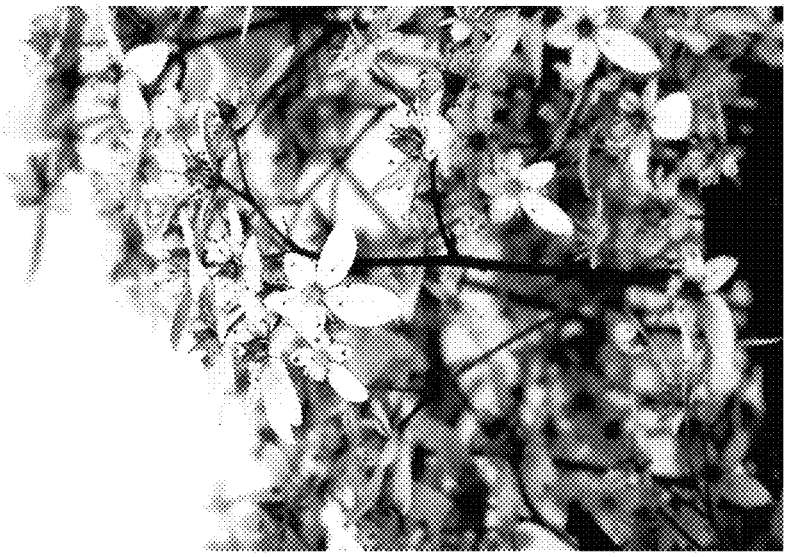

Botanical designation: *Saxifraga cortusifolia.*
Cultivar denomination: 'SH 1940'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 12, 2022, application number 2022/3063. Foreign priority is not claimed to this application.

BACKGROUND OF THE INVENTION

The present invention relates to a new and distinct cultivar of *Saxifraga* plant, botanically known as *Saxifraga cortusifolia* and hereinafter referred to by the name 'SH 1940'.

The new *Saxifraga* plant is a product of a planned breeding program conducted by the Inventor in Glandorf, Germany. The objective of the breeding program was to create new uniform *Saxifraga* plants with unique and attractive plant habit, leaf and flower coloration.

The new *Saxifraga* plant originated from a cross-pollination conducted by the Inventor in Glandorf, Germany in October, 2018 of a proprietary selection of *Saxifraga cortusifolia* identified as code number 18-62, not patented, as the female, or seed patent and a proprietary selection of *Saxifraga cortusifolia* identified as code number 18-123, not patented, as the male, or pollen parent. The new *Saxifraga* plant was discovered and selected by the Inventor as a single flowering plant from within the progeny of the stated cross-pollination grown in a controlled greenhouse environment in Glandorf, Germany in October, 2019.

Asexual reproduction of the new *Saxifraga* plant by in vitro axillary meristem culture in a controlled environment in Glandorf, Germany since May, 2020 has shown that the unique features of this new *Saxifraga* plant are stable and reproduced true to type in successive generations.

SUMMARY OF THE INVENTION

Plants of the new *Saxifraga* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SH 1940'. These characteristics in combination distinguish 'SH 1940' as a new and distinct *Saxifraga* plant:

1. Broadly upright and mounded plant habit.
2. Moderately vigorous to vigorous growth habit and moderate growth rate.
3. Dark green-colored leaves.
4. Freely flowering habit.
5. Creamy white-colored flowers that are held above the foliar plane.

Plants of the new *Saxifraga* differ from plants of the female parent selection in the following characteristics:

1. Leaves of plants of the new *Saxifraga* are lighter green in color than leaves of plants of the female parent selection.
2. Flowers of plants of the new *Saxifraga* are creamy white in color whereas flowers of plants of the female parent selection are pure white in color.

Plants of the new *Saxifraga* differ from plants of the male parent selection in the following characteristics:

1. Leaves of plants of the new *Saxifraga* are darker green in color than leaves of plants of the male parent selection.
2. Flowers of plants of the new *Saxifraga* are creamy white in color whereas flowers of plants of the male parent selection are greenish white in color.

Plants of the new *Saxifraga* can be compared to plants of *Saxifraga cortusifolia* 'SH 1925', disclosed in U.S. Plant Pat. No. 34,830. Plants of the new *Saxifraga* differ primarily from plants of 'SH 1925' in the following characteristics:

1. Leaves of plants of the new *Saxifraga* are lighter green in color than leaves of plants of 'SH 1925'.

2. Flowers of plants of the new *Saxifraga* are creamy white in color whereas flowers of plants of 'SH 1925' are purplish pink and purplish red in color.

BRIEF DESCRIPTION OF THE PHOTOGRAPHS

The accompanying colored photographs illustrate the overall appearance of the new *Saxifraga* plant showing the colors as true as it is reasonably possible to obtain in colored reproductions of this type. Colors in the photographs may differ slightly from the color values cited in the detailed botanical description which accurately describe the colors of the new *Saxifraga* plant.

Figure 1:
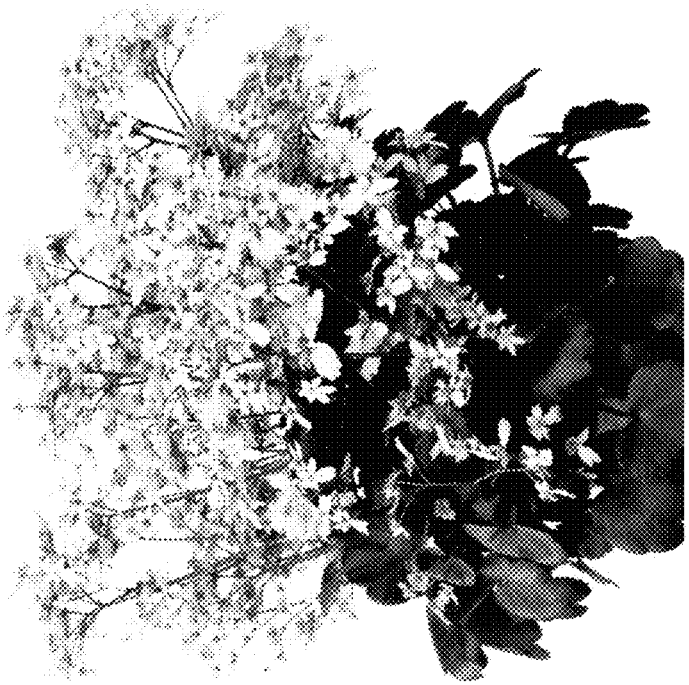

The photograph on left side of the first sheet (FIG. 1) is a side perspective view of a typical flowering plant of 'SH 1940' grown in a container.

The photograph on right side of the first sheet (FIG. 2) is a close-up view of a typical flowering plant of 'SH 1940'.

Figure 3:
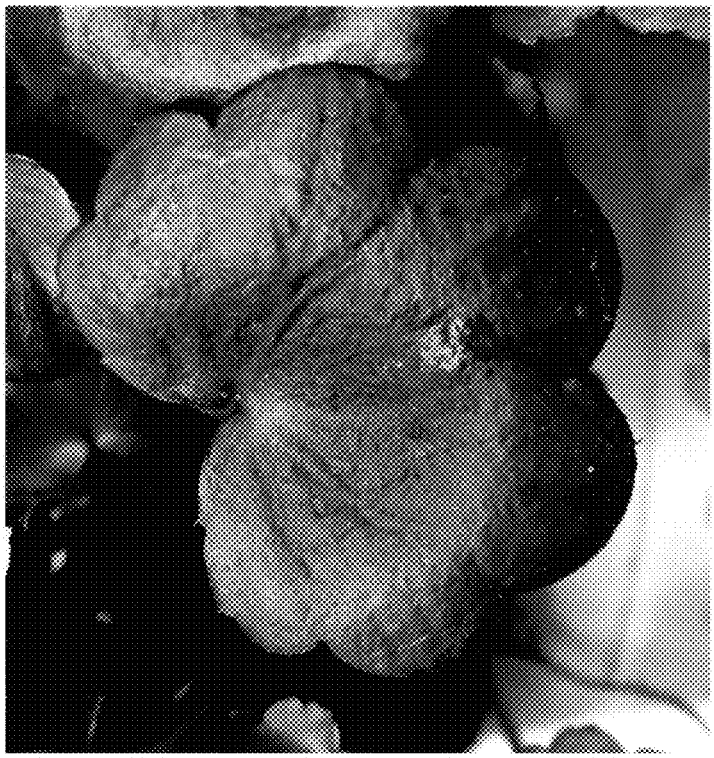

The photograph on the right side of the second sheet (FIG. 3) is a close-up view of the upper surface of a typical leaf of 'SH 1940'.

Figure 4:
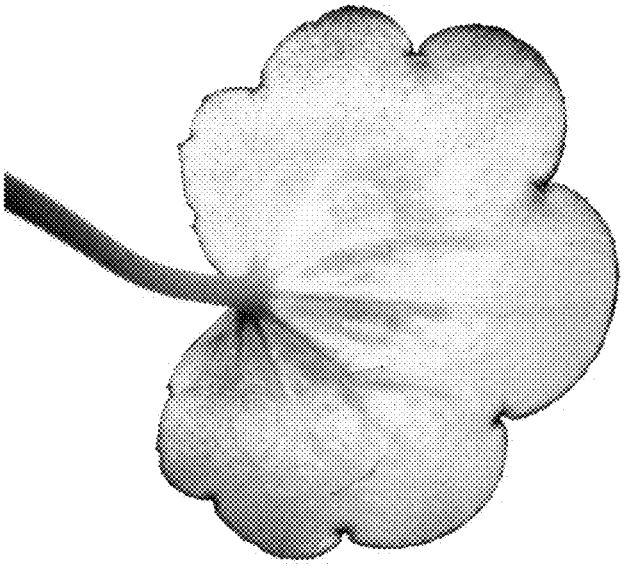

The photograph on the left side of the second sheet (FIG. 4) is a close-up view of the lower surface of a typical leaf of 'SH 1940'.

DETAILED BOTANICAL DESCRIPTION

The aforementioned photographs and following observations, measurements and values describe plants grown during the late autumn in 10.5-cm containers in an outdoor nursery in Glandorf, Germany and under cultural practices typical of commercial *Saxifraga* production. During the production of the plants, day temperatures ranged from 18° C. to 28° C. and night temperatures ranged from 14° C to 20° C. Plants were 24 weeks old when the photographs and the description were taken. In the following description, color references are made to The Royal Horticultural Society Colour Chart, 2015 Edition, except where general terms of ordinary dictionary significance are used.

Botanical classification: *Saxifraga cortusifolia* 'SH 1940'.

Parentage:

*Female, or seed, parent*.—Proprietary selection of *Saxifraga cortusifolia* disclosed as code number 18-62, not patented.

*Male, or pollen, parent*.—Proprietary selection of *Saxifraga cortusifolia* disclosed as code number 18-123, not patented.

Propagation:

*Type*.—In vitro axillary meristem culture.

*Time to produce a rooted young plant, summer*.—About four weeks at temperatures about 18° C. to 20° C.

*Root description*.—Fine to thick, fibrous; typically white to brownish in color; actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; broadly upright and mounding plant habit with flowers held above the foliar plane; overall plant shape, flattened globular; moderately vigorous to vigorous growth habit and moderate growth rate.

*Plant height, soil level to top of foliar plane*.—About 14 cm.

*Plant height, soil level to top of floral plane*.—About 27.8 cm.

*Plant diameter* (*area of spread*).—About 32.3 cm.

Leaf description:

*Arrangement*.—Leaves arranged in a basal rosette; alternate and single; about 15 basal leaves per plant.

*Length*.—About 5.6 cm.

*Width*.—About 6.9 cm.

*Shape*.—Reniform in outline; palmately lobed.

*Apex*.—Minutely and abruptly acute.

*Base*.—Truncate to deeply hastate, lobes free.

*Margin*.—Shallowly dentate to serrate and palmately lobed with about seven lobes per leaf; sinuses shallow to medium in depth and mostly parallel.

*Texture and luster, upper surface*.—Smooth, glabrous; slightly glossy.

*Texture and luster, lower surface*.—Smooth, glabrous; glossy.

*Venation pattern*.—Pinnate.

*Color*.—Developing leaves, upper surface: Close to 143A; lobe indentations, tinged with close to 183A. Developing leaves, lower surface: Close to 148C; lobe indentations, tinged with close to 181A. Fully developed leaves, upper surface: Close to NN137A to a blend of NN137A and 147A; lobe indentations, slightly tinged with close to 181A; narrow edges, close to 176B and 176C; venation, similar to lamina color. Fully developed leaves, lower surface: Close to 148C to 148D; lobe indentations, tinged with close to 182B; narrow edges, close to 178A; venation, close to 148D.

*Petioles*.—Length: About 10.5 cm. Diameter: About 4 mm. Strength: Weak. Texture and luster, upper and lower surfaces: Sparsely pubescent; slightly glossy. Color, upper and lower surfaces: Close to 148B. Color, lower surface: Close to 187B.

*Stipules*.—Quantity and arrangement: Two at the base of each petiole. Length: About 1.4 cm. Width: About 4 mm. Color, upper surface: Close to 146D to lighter than 146D. Color, lower surface: Close to 145D.

Flower description:

*Flower shape and habit*.—Rotate flowers arranged in terminal compound corymbs; freely flowering habit with about 90 flowers per inflorescence and about 1,000 flowers developing per plant; flowers face mostly upright to slightly outwardly.

*Fragrance*.—None detected.

*Natural flowering season*.—Plants begin flowering about 22 to 24 weeks after planting; plants flower naturally from the late summer into the winter in Germany.

*Flower longevity on the plant*.—About two weeks; flowers persistent.

*Flower buds*.—Length: About 3 mm. Diameter: About 3 mm. Shape: Globular. Texture and luster: Smooth, glabrous; matte. Color: Close to NN155D.

*Inflorescence height* (*including peduncle*).—About 25.1 cm.

*Inflorescence diameter*.—About 13.1 cm.

*Flower diameter*.—About 1.3 cm by 1.5 cm.

*Flower depth* (*height*).—About 6 mm.

*Petals*.—Quantity and arrangement: About five, occasionally 6 to 13, arranged in a single whorl or occasionally, in two whorls; upper three or four petals are smaller than lower one or two petals. Length, upper petals: About 4 mm to 11 mm. Width, upper petals: About 4 mm to 7 mm. Length, lower petals: About 11 mm to 18 mm. Width, lower petals: About 6 mm 15 mm. Shape, upper petals: Ovate. Shape, lower petals: Oblanceolate to elliptic. Apex, upper and lower petals: Bluntly acute to obtuse; with subsequent development, lower petal apices may become emarginate or two to three-lobed. Base, upper and lower petals: Attenuate. Margin, upper and lower petals: Entire; not undulate. Texture and luster, upper and lower petals, upper and lower surfaces: Smooth, glabrous; slightly velvety; matte. Color, upper and lower petals: When opening, upper and lower surfaces: Close to NN155D. Fully opened, upper and lower surfaces: Close to 157B; towards the margins, close to 157C; venation, similar to lamina colors; with subsequent development, color becoming closer to 145D.

*Sepals*.—Quantity and arrangement: Five, arranged in a single whorl. Length: About 3 mm. Width: About 1.5 mm. Shape: Ovate. Apex: Acute. Base: Cuneate. Margin: Entire. Texture and luster, upper surface: Smooth, glabrous; matte. Texture and luster, lower surface: Smooth, glabrous; slightly glossy. Color: When opening, upper and lower surfaces: Close to 144B. Fully opened, upper and lower surfaces: Close to 144B to 144C.

*Peduncles*.—Length: About 20.5 cm. Diameter: About 4 mm. Aspect: About 15 degrees from vertical; secondary peduncles, about 30 degrees from main peduncle axis. Strength: Moderately weak. Texture and luster: Smooth, glabrous; moderately glossy. Color: Close to 144B.

*Pedicels*.—Length: About 1.5 cm. Diameter: About 0.5 mm. Aspect: About 30 degrees from peduncle axis. Strength: Moderately strong. Texture and luster: Sparsely pubescent; slightly glossy. Color: Close to 144B, variably tinged with close to 181C.

*Reproductive organs*.—Stamens: Quantity per flower: About ten. Filament length: About 3 mm. Filament color: Close to NN155D. Anther shape: Double reniform. Anther size: About 0.3 mm by 0.4 mm. Anther color: Close to 61A. Pollen amount: Scarce. Pollen color: Close to 29A. Pistils: Quantity per flower: About two or occasionally, three or four. Pistil length: About 2 mm. Stigma diameter: About 0.2 mm. Stigma shape: Club-shaped. Stigma color: Close to 150C. Style length: About 1.7 mm. Style color: Close to 150B. Ovary color: Close to 150B. Floral bracts: Quantity per flower: One. Length: About 5 mm. Diameter: About 1.5 mm. Shape: Lanceolate. Apex: Narrowly acute. Base: Cuneate. Margin: Entire. Color, upper surface: Close to 146D and towards the base, close to 181A. Color, lower surface: Close to 146C and towards the base, close to 181A. Seeds and fruits: To date, seed and fruit development have not been observed on plants of the new *Saxifraga*.

Temperature tolerance: Plants of the new *Saxifraga* have been observed to tolerate temperatures ranging from about −7° C. to about 35° C. and to be suitable for USDA Hardiness Zones 8 through 11.

Pathogen & pest resistance: To date, plants of the new *Saxifraga* have not been observed to be resistant to pathogens and pests common to *Saxifraga* plants.

It is claimed:

1. A new and distinct *Saxifraga* plant named 'SH 1940' as illustrated and described.

* * * * *